(12) United States Patent
Tracey et al.

(10) Patent No.: US 8,583,256 B2
(45) Date of Patent: *Nov. 12, 2013

(54) SYSTEM AND METHOD FOR NERVE STIMULATION

(75) Inventors: Michael R. Tracey, Branchburg, NJ (US); Anthony DiUbaldi, Jackson, NJ (US)

(73) Assignee: Ethicon, Inc., Somerville, NJ (US)

( * ) Notice: Subject to any disclaimer, the term of this patent is extended or adjusted under 35 U.S.C. 154(b) by 121 days.

This patent is subject to a terminal disclaimer.

(21) Appl. No.: 13/094,644

(22) Filed: Apr. 26, 2011

(65) Prior Publication Data

US 2011/0264163 A1    Oct. 27, 2011

Related U.S. Application Data

(60) Division of application No. 11/146,522, filed on Jun. 7, 2005, now Pat. No. 7,979,137, which is a continuation-in-part of application No. 11/043,830, filed on Jan. 26, 2005, now abandoned.

(60) Provisional application No. 60/543,722, filed on Feb. 11, 2004.

(51) Int. Cl.
    *A61N 1/40*    (2006.01)
(52) U.S. Cl.
    USPC .............................................. 607/71; 607/41
(58) Field of Classification Search
    USPC ........................................................ 607/71
    See application file for complete search history.

(56) References Cited

U.S. PATENT DOCUMENTS

| | | |
|---|---|---|
| 3,683,915 A | 8/1972 | Voss |
| 3,902,502 A | 9/1975 | Liss et al. |
| 3,933,147 A | 1/1976 | DuVall et al. |
| 3,941,136 A | 3/1976 | Bucalo |
| 4,406,288 A | 9/1983 | Horwinski et al. |
| 4,537,195 A | 8/1985 | McDonnell |
| 4,719,922 A | 1/1988 | Padjen et al. |
| 4,909,255 A | 3/1990 | Farin |

(Continued)

FOREIGN PATENT DOCUMENTS

| | | |
|---|---|---|
| CN | 1593683 | 3/2005 |
| CN | 1745857 | 3/2006 |

(Continued)

OTHER PUBLICATIONS

Becker, T.J., "CardioMEMS Moves Closer to Commercializing its Innovative Heart Sensors", (Feb. 27, 2005) ATDC News & Information, Georgia Institute of Technology.

(Continued)

*Primary Examiner* — Luther Behringer
(74) *Attorney, Agent, or Firm* — Cheryl F. Cohen, LLC

(57) ABSTRACT

A system and method for stimulating a nerve, wherein the system includes a first waveform generator adapted to generate a first waveform having a frequency capable of stimulating a predetermined nerve of the mammal, a second waveform generator adapted to generate a carrier waveform having a frequency capable of passing through tissue of the mammal, a modulation device electrically coupled to the first and second waveform generators and adapted to modulate the first and carrier waveforms to create a modulated waveform, and an electrode electrically coupled to the modulation device and positioned substantially adjacent to skin of the mammal, and adapted to apply the modulated waveform thereto.

43 Claims, 10 Drawing Sheets

(56) References Cited

U.S. PATENT DOCUMENTS

| | | | |
|---|---|---|---|
| 4,989,605 A | 2/1991 | Rossen | |
| 5,167,237 A | 12/1992 | Rabin et al. | |
| 5,350,414 A | 9/1994 | Kolen | |
| 5,358,514 A * | 10/1994 | Schulman et al. | 607/61 |
| 5,421,817 A | 6/1995 | Liss et al. | |
| 5,458,630 A | 10/1995 | Hoegnelid et al. | |
| 5,464,434 A | 11/1995 | Alt | |
| 5,476,481 A | 12/1995 | Schondorf | |
| 5,487,759 A | 1/1996 | Bastyr et al. | |
| 5,556,421 A | 9/1996 | Prutchi et al. | |
| 5,558,640 A | 9/1996 | Pfeller et al. | |
| 5,562,717 A | 10/1996 | Tippey et al. | |
| 5,617,876 A | 4/1997 | van Duyl | |
| 5,645,062 A | 7/1997 | Anderson et al. | |
| 5,702,428 A | 12/1997 | Tippey et al. | |
| 5,722,996 A | 3/1998 | Bonnet et al. | |
| 5,730,125 A | 3/1998 | Prutchi et al. | |
| 5,735,887 A | 4/1998 | Barreras, Sr. et al. | |
| 5,791,344 A | 8/1998 | Schulman et al. | |
| 5,851,223 A | 12/1998 | Liss et al. | |
| 5,902,329 A | 5/1999 | Hoffmann et al. | |
| 5,984,854 A | 11/1999 | Ishikawa et al. | |
| 5,993,414 A | 11/1999 | Haller | |
| 6,035,236 A | 3/2000 | Jarding et al. | |
| 6,092,530 A | 7/2000 | Weissman et al. | |
| 6,099,479 A | 8/2000 | Christopherson et al. | |
| 6,155,267 A | 12/2000 | Nelson | |
| 6,164,284 A | 12/2000 | Schulman et al. | |
| 6,167,304 A | 12/2000 | Loos | |
| 6,183,461 B1 | 2/2001 | Matsuura et al. | |
| 6,199,575 B1 | 3/2001 | Widner | |
| 6,205,359 B1 | 3/2001 | Boveja | |
| 6,221,024 B1 | 4/2001 | Miesel | |
| 6,231,516 B1 | 5/2001 | Keilman et al. | |
| 6,240,317 B1 | 5/2001 | Villaseca et al. | |
| 6,263,246 B1 | 7/2001 | Goedeke et al. | |
| 6,285,897 B1 | 9/2001 | Kilcoyne et al. | |
| 6,298,272 B1 | 10/2001 | Peterfeso et al. | |
| 6,330,885 B1 | 12/2001 | Weissman et al. | |
| 6,354,991 B1 | 3/2002 | Gross et al. | |
| 6,360,129 B1 | 3/2002 | Ley et al. | |
| 6,366,814 B1 | 4/2002 | Boveja et al. | |
| 6,377,853 B1 | 4/2002 | Malaney et al. | |
| 6,384,353 B1 | 5/2002 | Huang et al. | |
| 6,402,689 B1 | 6/2002 | Scarantino et al. | |
| 6,404,204 B1 | 6/2002 | Farruggia et al. | |
| 6,413,393 B1 | 7/2002 | Van Antwerp et al. | |
| 6,432,050 B1 | 8/2002 | Porat et al. | |
| 6,438,407 B1 | 8/2002 | Ousdigian et al. | |
| 6,442,413 B1 | 8/2002 | Silver | |
| 6,443,883 B1 * | 9/2002 | Ostrow et al. | 600/14 |
| 6,447,462 B1 | 9/2002 | Wallace et al. | |
| 6,459,933 B1 | 10/2002 | Lurie et al. | |
| 6,471,645 B1 | 10/2002 | Warkentin et al. | |
| 6,497,655 B1 | 12/2002 | Linberg et al. | |
| 6,505,074 B2 | 1/2003 | Boveja et al. | |
| 6,535,766 B1 | 3/2003 | Thompson et al. | |
| 6,560,490 B2 | 5/2003 | Grill et al. | |
| 6,567,706 B2 | 5/2003 | Bar-Or et al. | |
| 6,652,449 B1 | 11/2003 | Gross et al. | |
| 6,662,052 B1 | 12/2003 | Sarwal et al. | |
| 6,668,191 B1 | 12/2003 | Boveja | |
| 6,701,185 B2 | 3/2004 | Burnett et al. | |
| 6,712,772 B2 | 3/2004 | Cohen et al. | |
| 6,751,501 B1 | 6/2004 | Schuler et al. | |
| 6,836,684 B1 | 12/2004 | Rijkhoff et al. | |
| 6,862,480 B2 | 3/2005 | Cohen et al. | |
| 6,879,859 B1 | 4/2005 | Boveja et al. | |
| 6,907,293 B2 | 6/2005 | Grill et al. | |
| 7,047,078 B2 | 5/2006 | Boggs, II et al. | |
| 7,054,690 B2 | 5/2006 | Irman | |
| 7,062,330 B1 | 6/2006 | Boveja et al. | |
| 7,310,557 B2 | 12/2007 | Maschino et al. | |
| 7,387,603 B2 | 6/2008 | Gross et al. | |
| 7,427,280 B2 | 9/2008 | Gerber | |
| 7,502,652 B2 | 3/2009 | Gaunt et al. | |
| 7,599,736 B2 | 10/2009 | DiLorenzo | |
| 7,676,271 B2 | 3/2010 | Wahlstrand et al. | |
| 7,815,895 B2 | 10/2010 | Katagiri et al. | |
| 8,170,683 B2 | 5/2012 | Wahlgren | |
| 2001/0018606 A1 | 8/2001 | Ingle et al. | |
| 2001/0025137 A1 | 9/2001 | Webb et al. | |
| 2001/0051768 A1 | 12/2001 | Schulman et al. | |
| 2002/0001870 A1 | 1/2002 | Oda et al. | |
| 2002/0011592 A1 | 1/2002 | Matsuo | |
| 2002/0026141 A1 | 2/2002 | Houben et al. | |
| 2002/0026244 A1 | 2/2002 | Trieu | |
| 2002/0082480 A1 | 6/2002 | Riff et al. | |
| 2002/0103514 A1 | 8/2002 | Abrahamson | |
| 2002/0107540 A1 | 8/2002 | Whalen et al. | |
| 2002/0111542 A1 | 8/2002 | Warkentin et al. | |
| 2002/0133196 A1 | 9/2002 | Thompson | |
| 2002/0151816 A1 | 10/2002 | Rich et al. | |
| 2003/0004403 A1 | 1/2003 | Drinan et al. | |
| 2003/0004553 A1 | 1/2003 | Grill et al. | |
| 2003/0162021 A1 | 8/2003 | van Heerden et al. | |
| 2003/0204224 A1 | 10/2003 | Torgerson et al. | |
| 2003/0212305 A1 | 11/2003 | Anderson et al. | |
| 2003/0220669 A1 | 11/2003 | Shealy | |
| 2003/0233137 A1 | 12/2003 | Paul | |
| 2004/0068203 A1 | 4/2004 | Gellman et al. | |
| 2004/0236194 A1 | 11/2004 | Meyer | |
| 2005/0177067 A1 | 8/2005 | Tracey et al. | |
| 2005/0277998 A1 | 12/2005 | Tracey et al. | |
| 2006/0047325 A1 | 3/2006 | Thimineur et al. | |
| 2006/0095090 A1 | 5/2006 | De Ridder | |
| 2006/0111756 A1 | 5/2006 | Chang | |
| 2006/0167500 A1 | 7/2006 | Towe et al. | |
| 2006/0178703 A1 | 8/2006 | Huston | |
| 2006/0195146 A1 | 8/2006 | Tracey et al. | |
| 2006/0229688 A1 | 10/2006 | McClure | |
| 2006/0247721 A1 | 11/2006 | Maschino | |
| 2007/0162085 A1 | 7/2007 | DiLorenzo | |
| 2007/0167990 A1 | 7/2007 | Mangrum et al. | |
| 2007/0185541 A1 | 8/2007 | DiUbaldi | |
| 2007/0219606 A1 | 9/2007 | Moreci et al. | |
| 2007/0233204 A1 | 10/2007 | Lima et al. | |
| 2007/0260288 A1 | 11/2007 | Gross | |
| 2008/0132962 A1 | 6/2008 | DiUbaldi et al. | |
| 2008/0132969 A1 | 6/2008 | Bennett et al. | |
| 2008/0147146 A1 | 6/2008 | Wahlgren et al. | |
| 2008/0161874 A1 | 7/2008 | Bennett et al. | |
| 2008/0293830 A1 | 11/2008 | Katagiri et al. | |
| 2009/0005713 A1 | 1/2009 | Podrazhansky et al. | |
| 2009/0048642 A1 | 2/2009 | Goroszeniuk | |
| 2009/0054952 A1 | 2/2009 | Glukhovsky et al. | |
| 2009/0062874 A1 | 3/2009 | Tracey et al. | |
| 2009/0093858 A1 | 4/2009 | DiUbaldi | |
| 2009/0132018 A1 | 5/2009 | DiUbaldi et al. | |
| 2009/0157149 A1 | 6/2009 | Wahlgren et al. | |
| 2009/0187230 A1 | 7/2009 | DiLorenzo | |
| 2010/0042018 A1 | 2/2010 | Kleinsinger | |
| 2010/0042180 A1 | 2/2010 | Mueller et al. | |
| 2010/0076533 A1 | 3/2010 | Dar et al. | |
| 2010/0249677 A1 | 9/2010 | DiUbaldi | |
| 2011/0264163 A1 | 10/2011 | Tracey et al. | |

FOREIGN PATENT DOCUMENTS

| | | |
|---|---|---|
| DE | 10033400 | 1/2001 |
| EP | 0783267 | 2/1999 |
| EP | 1048264 | 11/2000 |
| JP | 200316991 | 11/2000 |
| JP | 2001-259047 | 9/2001 |
| JP | 2003135607 | 5/2003 |
| WO | WO 90/14127 | 11/1990 |
| WO | WO 97/18856 | 5/1997 |
| WO | WO 97/39796 | 10/1997 |
| WO | WO 99/55411 | 11/1999 |
| WO | WO 00/33738 | 5/2000 |
| WO | WO 00/33065 | 6/2000 |
| WO | WO 01/49369 | 7/2001 |
| WO | WO 01/56633 | 8/2001 |
| WO | WO 02/22008 | 3/2002 |

(56) References Cited

FOREIGN PATENT DOCUMENTS

| WO | WO 02/27294 | 4/2002 |
|---|---|---|
| WO | WO 02/058551 | 8/2002 |
| WO | WO 02/062215 | 8/2002 |
| WO | WO 03/015625 | 2/2003 |
| WO | WO 03/020364 | 3/2003 |
| WO | WO 03/030733 | 4/2003 |
| WO | WO 03/071944 | 9/2003 |
| WO | WO 2004/050172 | 6/2004 |
| WO | WO 2005/002663 | 1/2005 |
| WO | WO 2005/079909 | 9/2005 |
| WO | 2007092301 | 8/2007 |

OTHER PUBLICATIONS

Chappel, J., Electronic News—Ambient Intelligence (Oct. 11, 2002).

Rousche, P.J. et al., "Flexible Polyimide-Based Intracortical Electrode Arrays with Bioactive Capacity", IEEE Transaction son Biomedical Engineering, vol. 48, No. 3 (2001) pp. 361-371.

Siwapornsathain, E. et al., "Telemetry and Sensor Platform for Ambulatory Urodynamics", Proceedings of the 2nd Annual Internaitonal IEEE-EMBS Special Topica Conference on Microtechnologies in Medicine & Biology, Madison, WI May 2002.

Voskerician, G. et al., "Biocompatability and biofouling of MEMS drug delivery devices", Biomaterials, 24 (2003) pp. 1959-1967.

Walter et al., "Evaluation of a 316LVM Woven Eye Electrode for Direct Bladder Stimulation", Engineering in Medicine and Biology, vol. 13, No. 4 (1991) pp. 1853-1854.

Fiber Optic Sensors, Product Datasheet FOP—M Pressure Sensor (undated).

Frost & Sullivan Report 2002.

Rosell, J. et al., "Skin Impedance from 1 Hz to 1 MHz", IEEE Transactions on Biomedical Engineering, vol. 35, No. 8, Aug. 1988, pp. 649-651.

Reilly, J, Patrick, "Electrical Stimulation and Electropathology", Cambridge University Press (1992).

Junge et al., "Titanium Coating of a Polypropylene Mesh for Hernia Repair: Effect on Biocompatability", Hernia vol. 6, No. 9, pp. 115-119, published on line Dec. 4, 2004.

Copending, co-owned U.S. Appl. No. 60/543,722, filed Feb. 11, 2004.

Copending, co-owned U.S. Appl. No. 61/211,197, filed Mar. 27, 2009.

Copending, co-owned U.S. Appl. No. 11/043,830, filed Jan. 26, 2005.

Copending, co-owned U.S. Appl. No. 11/146,522, filed Jun. 7, 2005.

Copending, co-owned U.S. Appl. No. 11/343,627, filed Jan. 31, 2006.

Copending, co-owned U.S. Appl. No. 11/344,285, filed Jan. 31, 2006.

Copending, co-owned U.S. Appl. No. 11/497,861, filed Aug. 2, 2006.

Copending, co-owned U.S. Appl. No. 12/661,949, filed Mar. 26, 2010.

English translation of Jun. 26, 2012 Office Action from Japanese Patent Office in counterpart Japanese Patent Application No. 2008-515738 (3 pages).

Co-owned, copending U.S. Appl. No. 11/866,588, filed Oct. 3, 2007.

\* cited by examiner

SYSTEM AND METHOD FOR NERVE STIMULATION

CROSS-REFERENCE TO RELATED APPLICATIONS

The present application is a division of U.S. patent application Ser. No. 11/146,522 filed on Jun. 7, 2005, now U.S. Pat. No. 7,979,137, which is a continuation-in-part of U.S. patent application Ser. No. 11/043,830, now abandoned, filed on Jan. 26, 2005, which claims priority to U.S. provisional application Ser. No. 60/543,722, filed. on Feb. 11, 2004, each of which is herein incorporated, by reference in their entirety.

BACKGROUND OF THE INVENTION

1. Field of the Invention

The present invention relates generally to devices and methods for stimulating nerves within the body, and more particularly to devices and method for stimulating the pudendal nerve.

2. Background Discussion

Women account for more than 11 million incontinence cases. One type of incontinence is stress urinary incontinence (SUI), where women experience involuntary loss of urine during normal daily activities and movements, such as laughing, coughing, sneezing and regular exercise. SUI may be caused by a functional defect of the tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Where stress incontinence is typically a result of an anatomical defect, another form of incontinence, urge incontinence, appears to be neurologically based and generally revealed as detrusor muscle instability or "bladder spasms." As such it is usually not conducive to surgical correction. Urge incontinence may or may not result in urine leakage, but both conditions otherwise have similar symptoms and similar forms of treatment, which generally include a combination of behavioral modification (learned strategies for reducing the urge sensation, scheduled voiding, avoidance of bladder-stimulating substances such as caffeine, and pelvic muscle exercises, with or without biofeedback) and drug therapy (typically anticholinergcic agents such as oxybutynin or tolterodine). These treatments require life-long therapy. Unfortunately, behavioral modification requires continuous effort to maintain results and the available drugs have significant side effects for many patients causing 80% to discontinue therapy within a year. The alternative therapy is to modify lifestyle to accommodate the condition—frequent urination to avoid "accidents" and wearing protective pads or undergarments, depending on the severity of the condition.

Another approach for treatment is stimulation of the sacral and/or pudendal nerve. The sacral spinal nerve roots separate in pairs to exit laterally through the nerve root foramina. The main destinations for these roots are the Isacral plexus. Nerves from this plexus provide the motor and sensory innervation of the lower limbs and pelvic organs. Specifically, the Sacral plexus splits into five sacral nerve pair, Sacral spinal nerves (S1 to S5). These nerves supply the thighs and lower parts of the legs, the feet, most of the external genital organs, and the area around the anus. The pudendal nerve is the largest branch of the pudendal plexus and is composed of somatosensory, somatomotor and autonomic elements derived from the anterior primary divisions of the second, third and fourth sacral nerves. The pudendal nerve is closer to the bladder, and its stimulation innervates the bladder, thus eliminating or lessening its contractions. At least one known commercial device stimulates the sacral nerve through a needle extended into the sacral nerve bundle. This device, however, supplies a continuous signal to provide constant stimulation of the nerve. Various drawbacks of this device include its invasive nature, and unwanted stimulation effects on other areas of the body, since the sacral nerve as a whole is being stimulated and multiple other areas of the body are innervated by such stimulation (i.e., resulting in leg twitches or the like).

A company called Advanced Bionics has an implantable stimulation device that targets the pudendal nerve specifically rather than the sacral nerve. This device is implanted in the vicinity of the pudendal nerve, but also is invasive and supplies a constant signal as described above and therefore, has the same drawbacks.

Accordingly, what is needed is an improved device and method for stimulating the pudendal nerve to treat incontinence.

SUMMARY OF THE INVENTION

The present invention provides a nerve stimulation device for use in a mammal including a first waveform generator adapted to generate a first waveform having a frequency capable of stimulating a predetermined nerve of the mammal, a second waveform generator adapted to generate a carrier waveform having a frequency capable of passing through tissue of the mammal, a modulation device electrically coupled to the first and second waveform generators and adapted to modulate the first and carrier waveforms to create a modulated waveform, and an electrode electrically coupled to the modulation device and positioned substantially adjacent to skin of the mammal, and adapted to apply the modulated waveform thereto.

The first and second waveform generators and the electrode may be positioned within a patch device having an adhesive thereon for securing the patch to the skin. In an alternate embodiment, the device further includes an electrically conductive gel extending from a position substantially in electrical contact with the electrode, through a tract in the mammal's tissue to a position closer to the predetermined nerve, which may be substantially adjacent to the predetermined nerve. In yet another embodiment, the predetermined nerve is the pudendal nerve, and the patch is positioned substantially at the abdominal or sacral regions of the mammal's body.

According to yet another embodiment, the first waveform has a frequency substantially within the range of 10-40 Hz, and may be a square wave. Further, the carrier waveform may have a frequency substantially within the range of 10-400 kHz, and may be a sinusoidal waveform.

In an alternate embodiment, the nerve stimulation device further includes a microprocessor adapted to control generation of the first and carrier waveforms by the first and second waveform generators. It may also further include a receiving device adapted to wirelessly receive biofeedback data, where the receiving device is electrically coupled to the microprocessor for providing the biofeedback data thereto. In yet another embodiment, the device further includes at least one biofeedback device implanted within the mammal's body, where the at least one biofeedback device includes at least one sensor device adapted to sense one or more physiological conditions within the mammal's body. The biofeedback device may also include at least one transmission device electrically coupled to the sensor device, with the biofeedback device being adapted to receive signals from the sensor device and wirelessly transmit to a point external of the mammal's body biofeedback data representing the signals. In yet a further embodiment, the biofeedback data is transmitted to the microprocessor via the receiver device, and the microprocessor controls the first and second waveforms generators based at least in part on the biofeedback data. In different embodiments, the biofeedback data could represent bladder pressure and/or abdominal pressure.

The present invention also provides a method for stimulating a predetermined nerve of a mammal including generating a first waveform having a frequency capable of stimulating the predetermined nerve, generating a carrier waveform having a frequency capable of passing through tissue of the mammal, modulating the first waveform with the carrier waveform to produce a modulated signal, and applying the modulated signal to the mammal's skin.

The method may further include implanting at least one sensor within the mammal's body, using the implanted sensor sensing one or more physiological properties within the body, wirelessly transmitting biofeedback data representing the sensed physiological properties, and using the biofeedback data to control generation of the first and carrier waveforms by the first and second waveform generators.

Also provided is a nerve stimulation device including a first waveform generator adapted to generate a first waveform having a frequency substantially within the range of 10-40 Hz, a second waveform generator adapted to generate a carrier waveform having a frequency substantially within the range of 10-400 KHz, a modulation device electrically coupled to the first and second waveform generators for modulating the first and carrier waveforms to thereby create a modulated waveform, and an electrode electrically coupled to the modulation device and positioned substantially adjacent to the skin of a mammal for applying the modulated waveform to the skin of the mammal.

These and other features and advantages of the present invention will become apparent from the following more detailed description, when taken in conjunction with the accompanying drawings which illustrate, by way of example, the principles of the invention.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, although the present invention is described in detail in relation to the nerve stimulation in females, it is to be understood that it can be readily adapted for use in males. Further, the inventive principles, apparatus and methods disclosed herein may also have application for stimulating various other nerves, such as stimulation of nerves during labor and delivery. In addition, the technology described herein can be applied to various components of the nervous system that contribute or effect the following conditions: Stress urinary incontinence, anal and fecal incontinence, sexual dysfunction, interstitial cystitis, chronic pain such as but not limited to pelvic pain and nocturia.

One unique aspect of the invention, described herein is the manner in which the pudendal nerve is stimulated, which is transdermally rather than via a needle or other invasive element inserted within the body in close proximity to the nerve. This has obvious advantages in comfort for the patient, but also eliminates the surgical risk of mistakenly injuring other nerves or vessels. The system provides direct, but preferably selective stimulation to the pudendal nerve that is controlled in part based on biofeedback data corresponding to physiological conditions sensed in the body, such as bladder contractions.

As indicated above, it is known that surface electrodes can be used to stimulate both nerves and muscles within the body. One problem that is encountered, however, is that the applied electrical signals tend to spread widely, affecting untargeted muscles and nerves as well as targeted ones, which is often undesirable. Further, to account for this signal dissipation, the applied current levels must be significantly increased to ensure adequate current densities at the targeted site. Another challenge associated with transdermal application of electrical signals is the fact that the pudendal nerve is stimulated by a low frequency signal, on the order of 10-40 Hz. Such a low frequency signal, however, cannot itself pass through body tissue, and therefore is not conducive to direct transdermal application. Many of these challenges have been overcome by the present invention, which will now be described in detail.

Figure 1:
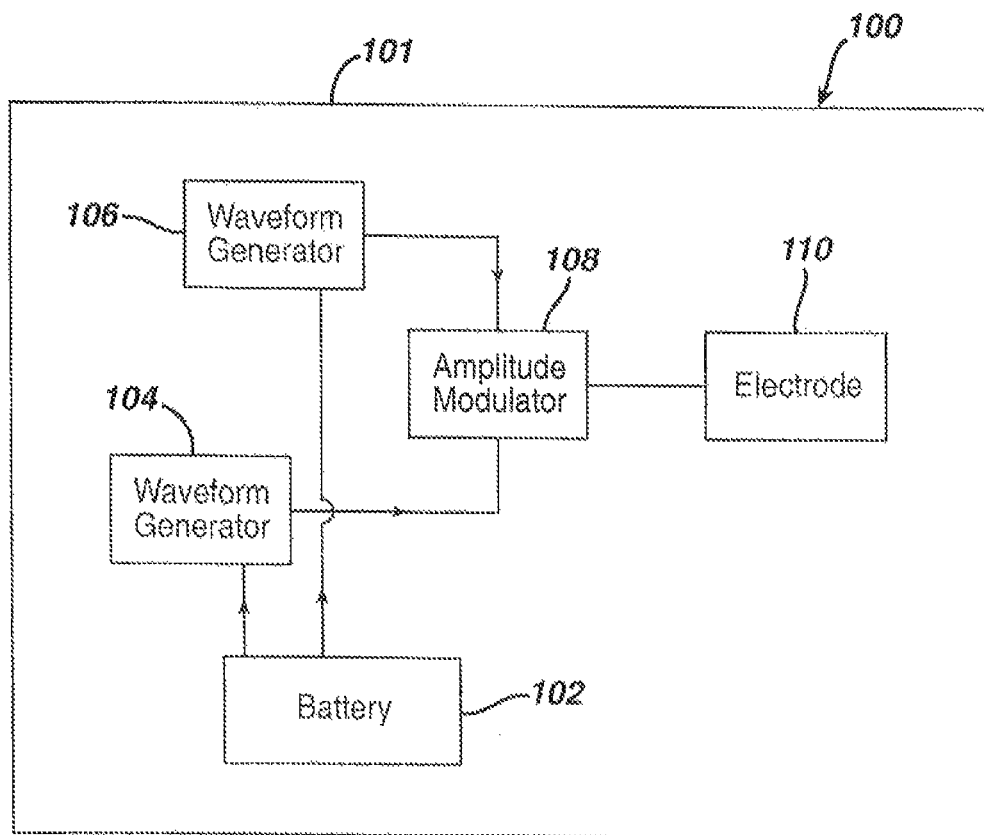
FIG. 1 is a schematic illustration of a transdermal transmission device according to one embodiment of the present invention.

FIG. 1 illustrates schematically an exemplary transdermal signal transmission device 100 in accordance with the present invention. The signal transmitter is preferably contained within a transdermal patch 101 or the like that can be removably secured to the surface of the skin, preferably in the lower abdominal region or lower sacrum of the patient. The patch may be any suitable adhesive bandage or the like.

Figure 2:
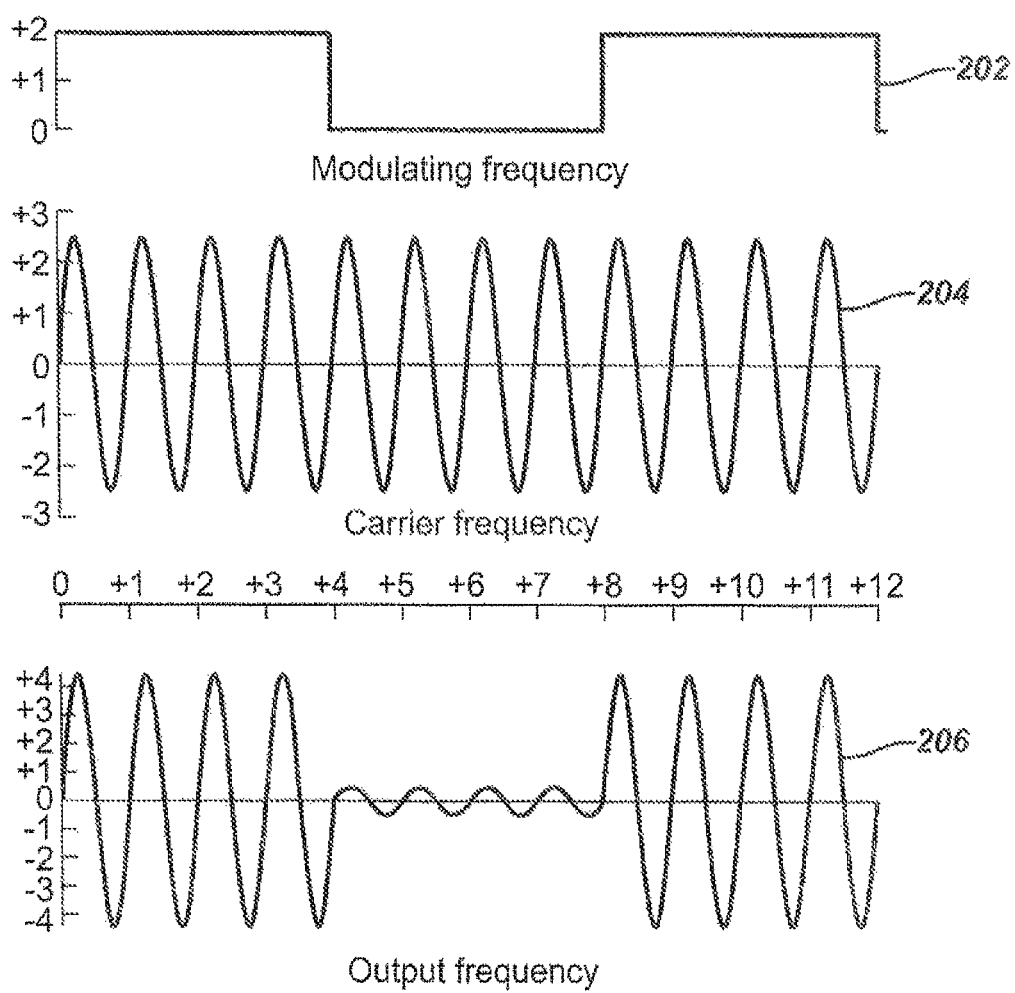
FIG. 2 illustrates exemplary waveforms generated by the device of FIG. 1.

The signal transmitter 100 includes a suitable power source 102 such as a lithium ion film battery by CYMBET™ Corp. of Elk River, Minn., model number CPF141490L, and first 104 and second 106 waveform generators that are electrically coupled to and powered by the battery. These waveform generators may be of any suitable type, such as those sold by Texas Instruments of Dallas, Tex. under model number NE555. The first waveform generator 104 generates a first waveform or signal having a frequency known to stimulate nerves in the body, including the pudendal nerve, which is approximately within the range of 10-30 Hz. As indicated above, such a low frequency signal applied to the skin, in and of itself, cannot pass through body tissue to reach the pudendal nerve with sufficient current density to stimulate the nerve. Thus, the second waveform generator 106 is provided to generate a carrier waveform, which is applied along with the first waveform to an amplitude modulator 108, such as an On-Semi MC1496 modulator by Texas Instruments. The first waveform is preferably a square wave having a frequency of approximately 10-40 Hz, and the second waveform is preferably a sinusoidal signal having a frequency in the range of 10-400 KHz. As those skilled in the art will readily recognize, modulation of this first waveform 202 with the second waveform (carrier wave) 204 results in a modulated waveform or signal 206 having generally the configuration shown in FIG. 2.

The modulated signal 206 is provided to an appropriate surface electrode 110, such as DURA-STICK Self Adhesive Electrodes from Chattanooga Group, Inc. of Hixson, Tenn., that applies the modulated waveform directly to the skin. As is readily understood by those skilled in the art, the use of the modulated signal enables transmission of the waveform through tissue due to the high frequency nature of the first waveform, yet allows it to be detected (and responded to) by the pudendal nerve due to the low frequency envelope of the modulated signal.

In one embodiment, the conductance of the stimulation energy from the surface electrode to the target nerve can be increased by the placement of a conductive tract that may extend either fully or partially from the surface electrode to the target nerve. The conductive tract may be a cross-linked polyacrylamide gel such as the Aquamid® injectable gel from Contura of Denmark. This bio-inert gel, injected or otherwise inserted, is highly conductive and may or may not be an aqueous solution. The implanted gel provides benefits over rigid implants like wire or steel electrodes. Some of those advantages include ease of delivery, less invasive and patient comfort as the gel is not rigid and can conform to the patients body. As stated above, the clear advantage of the injected gel tract is a highly conductive path from the surface electrode to the target nerve that is much more conductive than the surrounding tissue. This reduces energy dispersion and increases the efficiency of the energy transfer between the surface electrode and the target nerve.

The above-described signal transmission device is preferably used in a system that incorporates various biofeedback mechanisms to both create a closed-loop system for treating urge incontinence, but also to provide a system wherein pudendal nerve stimulation is selective, and applied only when necessary as opposed to constantly as has been the case with known attempts at pudendal nerve stimulation. Such a system further includes one or more sensor devices 115 that are preferably implanted within the body. The sensor devices preferably include at least one sensor 120 (FIG. 3) that will sense a selected bio-physiological property, and a data transmission device 122 that transmits data or information gathered by the sensor back outside the body to be further processed as described more fully below.

Figure 3:
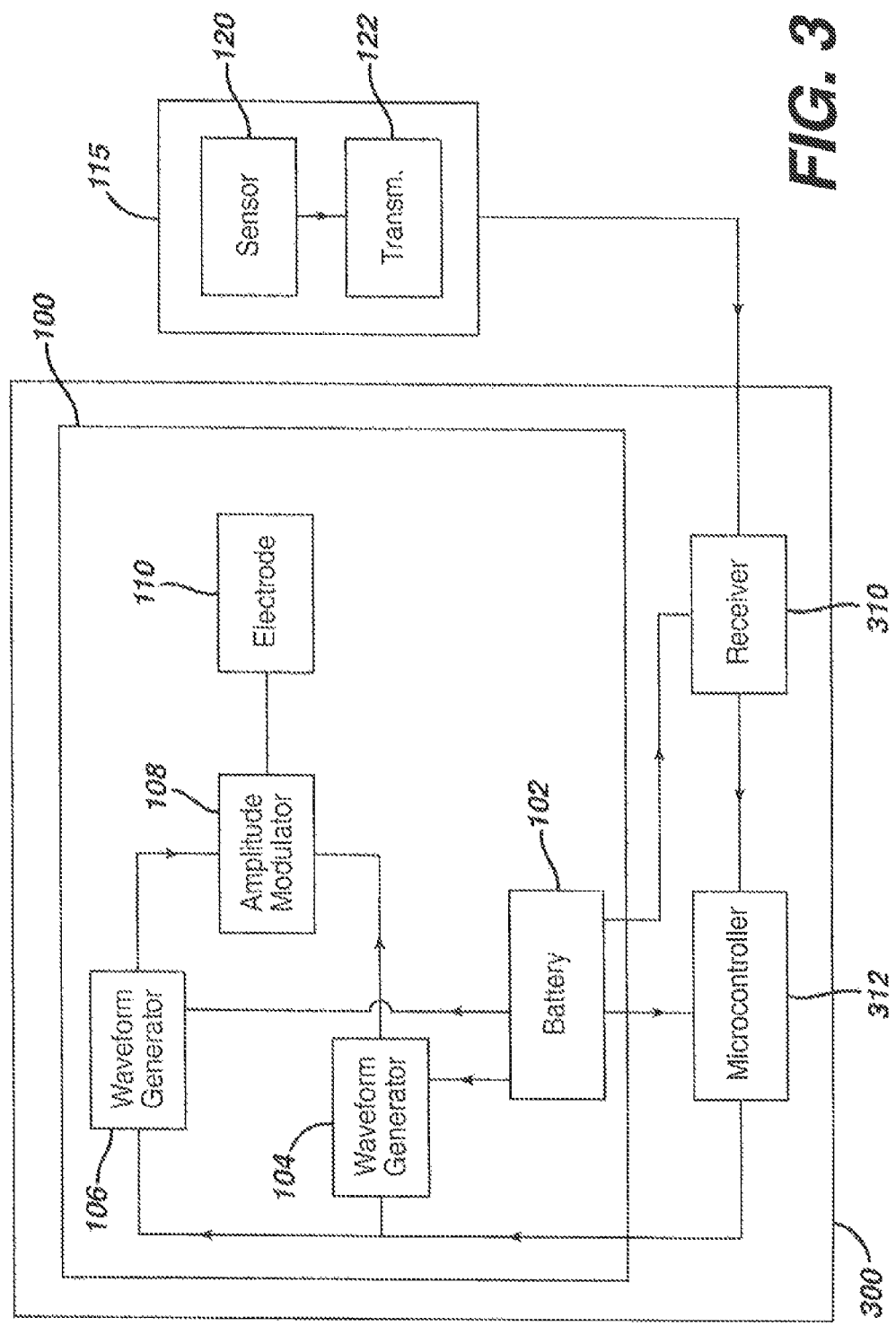
FIG. 3 is a schematic illustration of the device of FIG. 1 further incorporating a biofeedback mechanism.

Referring now to FIG. 3, signal transmitter 100 is part of a larger signal control device 300 that further includes a receiving device 310 such as a MAX1472 from Maxim Semiconductors of Sunnyvale, Calif., that is electrically coupled to and powered by the battery 102. The receiving device receives data from the one or more sensors 115 and provides this data to a microcontroller 312 or the like. The microcontroller is programmed to receive and analyze the data, and based on this data to provide input to the first and second waveform generators 104, 106 to thereby control signal transmission by the signal transmitter 100. For example, the biofeedback sensor 115 may be a pressure sensor that is implanted within the bladder as described in detail below. As pressure measured within the bladder over time is indicative of the existence and magnitude of bladder contractions, when such measurements indicate spastic bladder muscle activity (as compared to normal bladder contractions which will result in a slow and steady rise of pressure within the bladder), a feedback signal can be transmitted to the receiving device and subsequently to the microcontroller. Based on receipt of this signal, the microcontroller will, via control of the waveform generators, cause the electrode to transmit the modulated signal. Receipt of the signal by the pudendal nerve will innervate the bladder muscles to substantially eliminate the spastic muscle contractions.

Figure 4:
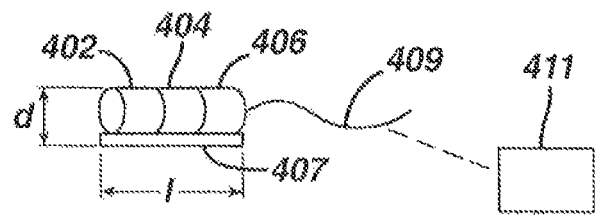
FIG. 4 illustrates an exemplary implantable sensor device that can be used in conjunction with the device of FIG. 3.
Figure 5A:
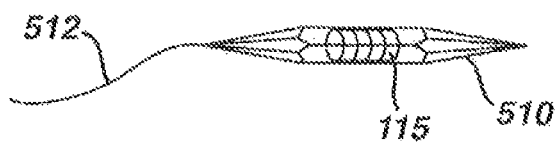
FIG. 5a illustrates the sensor device of FIG. 4 within an expandable cage in its non-expanded state.
Figure 5B:
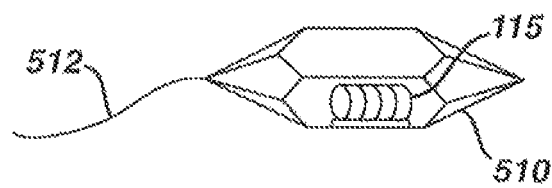
FIG. 5b illustrates the sensor device of FIG. 4 within an expandable cage in the expanded state.

Referring now to FIGS. 4, 5a and 5b, exemplary biofeedback devices 115 will now be described in greater detail. In a preferred embodiment, the implantable biofeedback device 115 consists of multiple electronic components including a power source 402, one or more sensor components 404, and an electronic interface 406, each of which are electrically coupled to one another and mechanically mounted on a printed circuit board 407 in a manner well known in the art. The one or more sensor components 404 sense predetermined physiological properties within the body, and transmit signals or data representing such properties to the electrical interface 406. The system may include a data storage element for storing data correlating to the sensed physiological properties, but may also include a transmitter 409 for transmitting the data external of the patient's body so that it can be used to control generation of the modulated signal as described above. As shown in both FIGS. 5a and 5b, in one embodiment the biofeedback device 115 is substantially surrounded by a collapsible housing 510 or cage.

Preferably, the biofeedback system (exclusive of the housing) has an overall size of about 0.65-10 mm in diameter d, and about 0.65-10 mm in length l. In a preferred embodiment, the sensor component is a micro-miniature piezo-resistive pressure transducer for measuring pressure within a patient's bladder. A suitable transducer is an MPX series pressure sensor from Motorola of Schaumburg, Ill. Other suitable components may include the MSP430F149 microcontroller from Texas Instruments, Inc. of Dallas, Tex. that can be used, to acquire, filter and store data from the pressure sensor, and power source such as any suitable biocompatible lithium battery. Although particular suitable electronic components have been named above, many others also exist and could be incorporated into the present invention. As indicated, the electronic components are preferably mounted on printed circuit board. Subsequently, the components and circuit board can be covered or encapsulated in silicone or other suitable covering to protect them from the environment, such as the fluid environment in the bladder Referring now again to the housing 510 as illustrated in greater detail in FIGS. 5a and 5b, in a preferred embodiment the housing is a collapsible cage made of a suitable metal such as Nitonol, stainless steel, or a titanium alloy, or a suitable biocompatible polymer such as polypropylene or polyethylene terapthalate. The collapsible cage is advantageous in that it can exist in a collapsed state shown in FIG. 5a that is sufficiently small to allow insertion through the patient's urethra. Once inserted into the bladder as will be described further below, however, the cage can assume the expanded state shown in FIG. 5*b*, which has a size sufficiently large so that it cannot pass back into the urethra, and thus will remain in the bladder until physical removal is desired. The housing or cage returns to its expanded state (FIG. 5*b*) when not compressed by an external force. The electrical components and printed circuit board can be mechanically affixed to the cage in any suitable manner, such as by using a biocompatible adhesive. The housing may further include a tail element 512 extending outwardly therefrom. This tail element 512 may operate as the transmitter for the device in place of the transmitter configuration shown in FIG. 4. As will be further described below, this tail element 512 may also incorporate additional sensor elements if desired.

In another embodiment, the expandable cage may be made of an absorbable material such as Ethisorb® (an absorbable synthetic composite made from polyglactin and polydioxanon) from Ethicon, Inc. of Somerville, N.J., or a combination of absorbable and non-absorbable materials. The absorbable material would preferably dissolve after a predetermined period of time, such as at least 2-3 days, so that the implantable device could be used for temporary data acquisition and subsequently expelled from the body in a non-invasive manner after sufficient data has been gathered.

Figure 6:
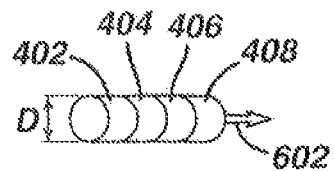
FIG. 6 illustrates an alternate embodiment of an implantable sensor device.

As an alternative to the collapsible cage described above, the housing could have a stable structure rather than a collapsible structure that itself has an outer diameter D that is smaller than the diameter of the urethra to allow insertion therethrough into the bladder (see FIG. 6). The housing may further have one or more projections 602, such as screw threads, barbs or the like, extending outwardly therefrom that can be attached to the sidewall of the bladder by being pushed or driven therein. In yet other alternate embodiments, the implantable device could be sutured to the bladder wall, or adhered thereto using a suitable biocompatible adhesive.

Figure 7A:
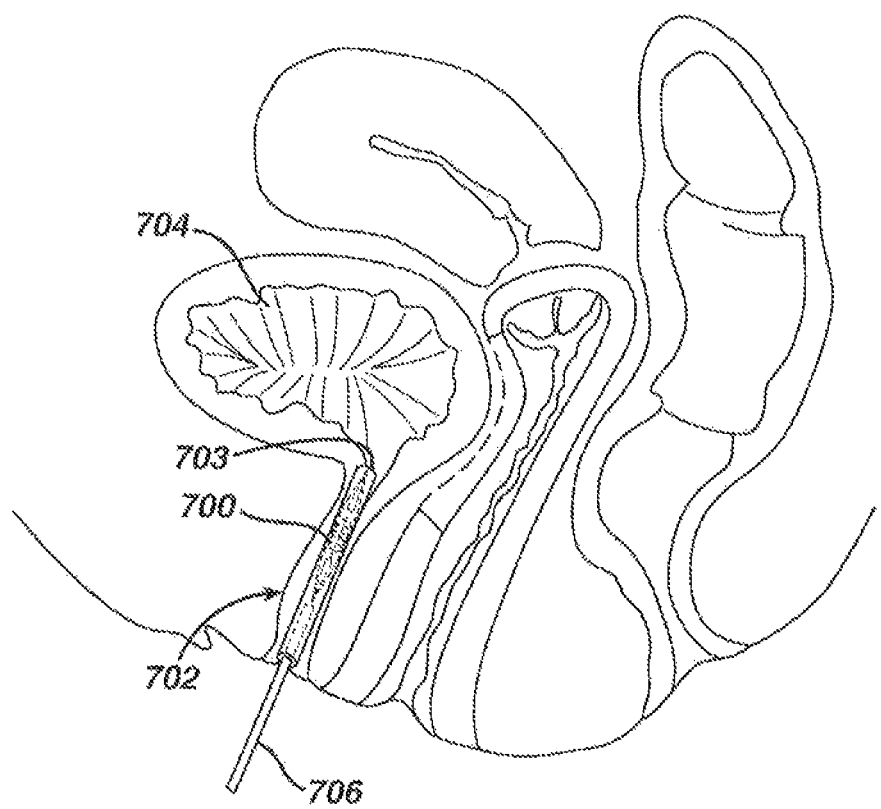
FIGS. 7a-7c illustrate various steps of deployment of the implantable sensor device of FIGS. 5a and 5b.
Figure 7B:
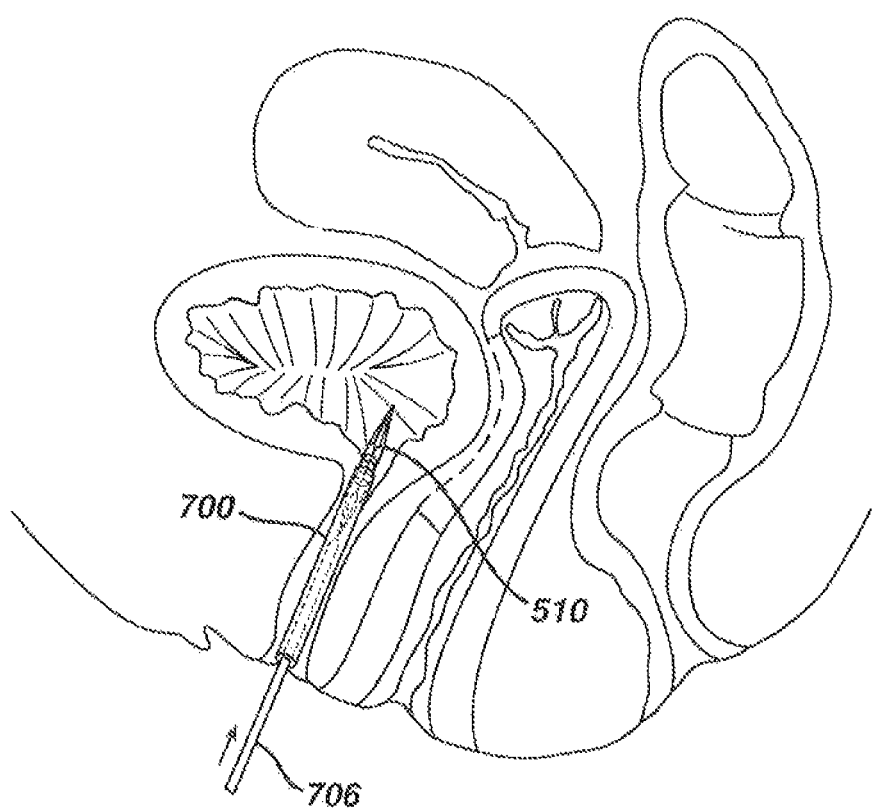
Figure 7C:
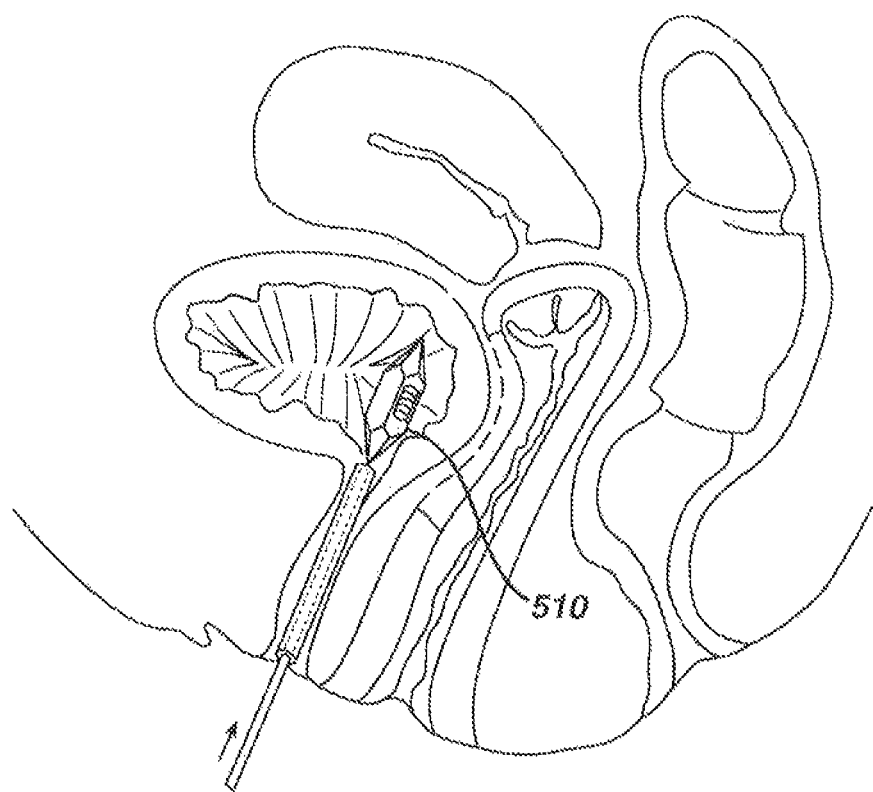
Figure 8:
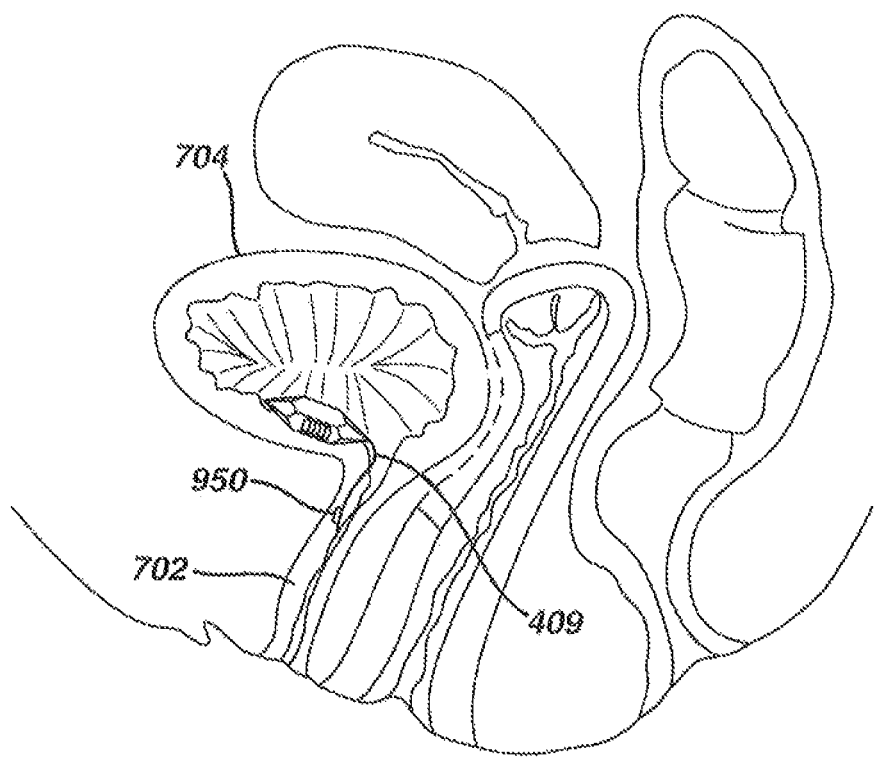
FIG. 8 illustrates the implantable sensor device of FIGS. 5a and 5b deployed within the bladder and having a tail extending into the urethra.

In order to implant the device 115, the housing 510 is compressed and loaded into a single or multi-lumen catheter 700 as shown in FIG. 7*a*, which is inserted through the urethra 702 until the tip or distal end 703 is positioned within the bladder 704. The catheter may be any catheter suitable for intra-urethral applications, such as a Foley catheter. Fluoroscopy, ultrasound or other similar technology known to those skilled in the art may be used to aid in delivery and placement of the implantable system within the bladder. If a multi-lumen catheter is used, other lumens may be used to fill or drain the bladder, deliver drugs, provide an access for visualization, or monitor pressure while placing the implantable system. An expulsion element 706, such as a push rod or the like is inserted into the primary lumen behind the device and housing, and once the distal end of the catheter is properly positioned within the bladder, the expulsion element is moved toward the distal end of the catheter in the direction of the arrow as shown in FIGS. 7*b* and 7*c* to thereby expel the device and housing from the distal end of the catheter and into the bladder. As the implantable system exits the catheter, the collapsible cage 510 is no longer being held in its collapsed state, and proceeds to expand to its fully expanded state. Although use of a catheter is described, other suitable implantation methods may also be used, such as placement via the working channel in a cystoscope or similar surgical tool, or placement via laparoscopic or open surgical methods. Once deployed within the bladder, the expandable cage is dimensioned to prevent the device from being lodged in the bladder neck or otherwise passing into the urethra, but further allows urine to freely flow through it. FIG. 8 illustrates the device fully deployed within the bladder 704.

As mentioned above, alternate embodiments that do not employ expandable cages may also be suitable, such as that shown in FIG. 6. The method of implantation of such devices would be similar to that described above, with the expulsion element within the catheter being used to drive the projecting element 602 into the wall of the bladder to thereby anchor the device to the bladder.

For purposes of the present invention, the device 115 would preferably remain within the bladder for an extended period of time to provide constant feedback used to control operation of the electrode. Where constant feedback is not used (i.e., FIG. 1), the implantable sensors described herein may nevertheless be used to obtain data useful in rendering an accurate diagnosis and/or appropriate treatment. For example, the device could remain within the bladder for 1-2 days, with bladder pressure measurements being taken every ½ second. The type and frequency of bladder pressure changes can be subsequently analyzed to provide feedback to assess urinary function. For example, vesicle pressure measured over time can reveal voiding times and frequency, can provide an indication of an overactive bladder, or of bladder overfilling. In one embodiment, the sensor element(s) are designed to operate in an extended sleep mode, "waking up" at fixed intervals of time to measure pressure or the like. Once sufficient data has been gathered, the device can subsequently be removed from the bladder by inserting a catheter into the bladder to retrieve the implantable device, or using the operating channel of a cystoscope or other suitable instrument to retrieve the device. The catheter or cystoscope would be inserted into the bladder, and the device grasped and pulled back into the catheter or cystoscope channel and subsequently removed from the body.

Under these circumstances, the biofeedback device may further incorporate a data storage device 408 (FIG. 4) in addition to or in place of the transmitter for storing rather than transmitting the data. The data can be subsequently retrieved and manipulated, preferably by uploading the data to a PC based software application in any suitable manner, such as wirelessly, for example, via an infrared data acquisition unit such as ENDEC HSDL-7001 and an IrDA transceiver HSDL-3202 interfaced to the microprocessor, via radiofrequency acquisition, or via a hard wire connection such as through an RS232 interface.

Figure 9:
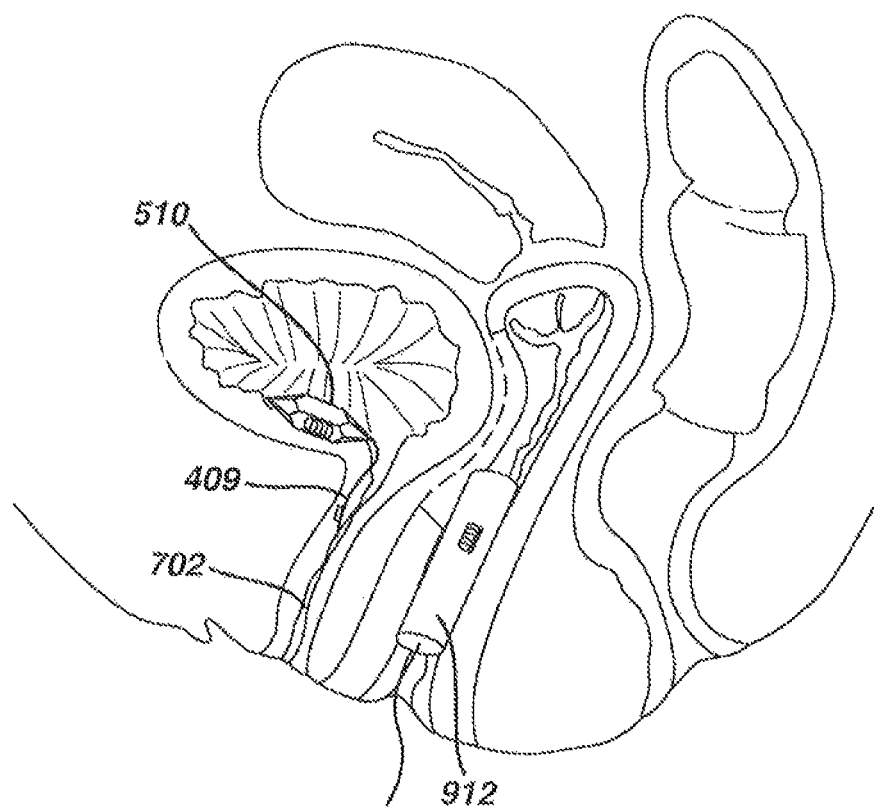
FIG. 9 illustrates first and second implantable sensor devices that can be used in conjunction with the system of FIG. 3.

Referring again to FIG. 3, where biofeedback data is utilized, receiver 310 may receive feedback data from more than one biofeedback device 115. In one embodiment shown in FIG. 9, a second implantable sensor device 902 similar to that shown and described in conjunction with FIG. 4 is designed for insertion into the vaginal canal of a patient, and thus is preferably encapsulated in a "tampon-like" device or casing as shown. This casing 912 is preferably simply rolled up or bound cotton, similar to a tampon. With the second implantable device sensing abdominal pressure, and the first implantable device sensing bladder pressure, the detrusor pressure (pressure of the muscle lining of the wall of the bladder tissue) can be determined by subtracting the bladder pressure from the abdominal pressure. Rises in detrusor pressure will occur if the patient strains, coughs, sneezes, laughs, etc., and detection of these pressures are clinically significant in the diagnosis of various bladder and lower urinary tract disease states. For example, the frequency of detrusor pressure increases provides meaningful data for assessing urge incontinence.

In an alternate embodiment, one of the two implantable devices transmits data to the other, which then wirelessly transmits both sets of data to receiver 310.

Figure 10A:
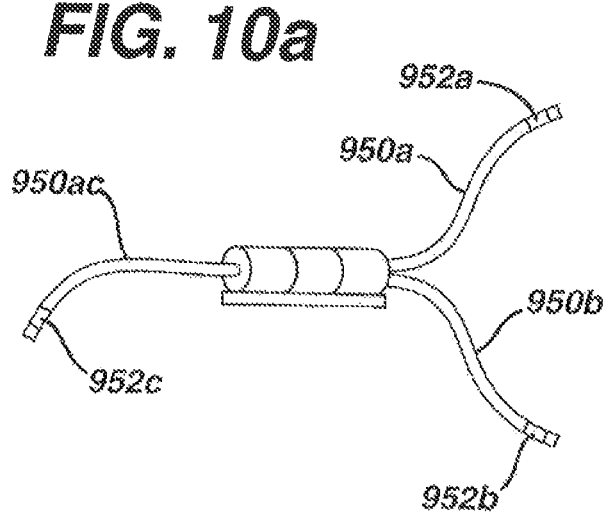
FIG. 10a illustrates an alternate embodiment of an implantable sensor device.
Figure 10B:
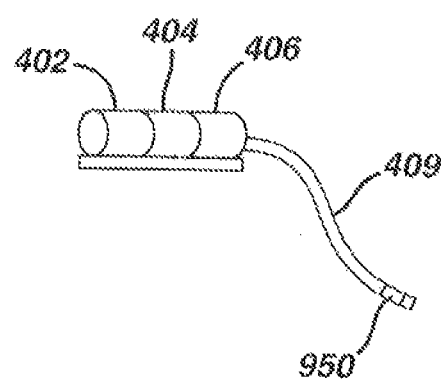
FIG. 10b illustrates yet another embodiment of an implantable sensor device.

In yet another embodiment, the first implantable device within the bladder further includes one or more additional sensors 950 that are incorporated into one or more tail elements, as shown in FIGS. 10 and 10*a*. In one particular implementation, the sensor(s) are leak detection sensors incorporated into a tail that is designed to extend from the device within the bladder, through the sphincter and into the urethral canal 702 as shown in FIG. 8. This sensor(s) detect the presence of fluid, and thus will detect leakage of urine such as occurs in a stress incontinent patient, while at the same time the pressure sensor within the bladder measures bladder pressure. Thus, stress incontinence episodes can be recorded by correlating time at which a rise in bladder pressure occurs concurrently with detection of fluid leakage through the urethra.

Further, multiple tail elements 950*a*, 950*b*, 950*c* may incorporate multiple sensor elements 952*a*, 952*b*, 952*c* as shown in FIG. 10*a* to record the pressure at different points in the bladder, and thus provide more accurate readings.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A nerve stimulation device for a mammal comprising:
    a first waveform generator adapted to generate a first waveform having a frequency capable of stimulating a predetermined nerve of the mammal;
    a second waveform generator adapted to generate a carrier waveform having a frequency capable of passing through tissue of the mammal;
    an amplitude modulation device electrically coupled to the first and second waveform generators and adapted to multiply the first and carrier waveforms to create a modulated waveform that maintains a modulation envelope and frequency information of the first waveform and the carrier waveform and the carrier waveform; the modulated waveform is capable of transdermally electrically stimulating the predetermined nerve; and
    an electrode electrically coupled to the modulation device and positioned substantially adjacent to skin of the mammal, and adapted to apply the modulated waveform thereto.

2. The nerve stimulation device according to claim 1, wherein the first and second waveform generators and the electrode are positioned within a patch device having an adhesive thereon for securing the patch to the skin.

3. The nerve stimulation device according to claim 1, further comprising an electrically conductive gel extending from a position substantially in electrical contact with the electrode, through a tract in the mammal's tissue to a position closer to the predetermined nerve.

4. The nerve stimulation device according to claim 3, wherein the electrically conductive gel extends to a position within the mammal's body that is substantially adjacent to the predetermined nerve.

5. The nerve stimulation device according to claim 1, wherein the predetermined nerve is the pudendal nerve, and the patch is positioned substantially at the abdominal or sacral regions of the mammal's body.

6. The nerve stimulation device according to claim 1, wherein the first waveform has a frequency substantially within the range of 10-40 Hz.

7. The nerve stimulation device according to claim 6, wherein the first waveform is a square wave.

8. The nerve stimulation device according to claim 7, wherein the carrier waveform has a frequency substantially within the range of 10-400 kHz.

9. The nerve stimulation device according to claim 8, wherein the carrier waveform is a sinusoidal waveform.

10. The nerve stimulation device according to claim 1, further comprising a microprocessor adapted to control generation of the first and second carrier waveforms by the first and second waveform generators.

11. The nerve stimulation device according to claim 10, further comprising a receiving device adapted to wirelessly receive biofeedback data, the receiving device being electrically coupled to the microprocessor for providing the biofeedback data thereto.

12. The nerve stimulation device according to claim 11, further comprising at least one biofeedback device implanted within the mammal's body, the at least one biofeedback device including at least one sensor device adapted to sense one or more physiological conditions within the mammal's body.

13. The nerve stimulation device according to claim 12, wherein the biofeedback device further includes at least one transmission device electrically coupled to the sensor device, the biofeedback device being adapted to receive signals from the sensor device and wirelessly transmit to a point external of the mammal's body biofeedback data representing the signals.

14. The nerve stimulation device according to claim 13, wherein the biofeedback data is transmitted to the microprocessor via the receiver device, and wherein the microprocessor controls the first and second waveforms generators based at least in part on the biofeedback data.

15. The nerve stimulation device according to claim 13, wherein the biofeedback data represents bladder pressure.

16. The nerve stimulation device according to claim 13, wherein the biofeedback data represents abdominal pressure.

17. A method for stimulating a predetermined nerve of a mammal comprising:
    generating a first waveform laving a frequency capable of stimulating the predetermined nerve;
    venerating a carrier waveform having a frequency capable of passing through tissue of the mammal;
    amplitude modulating said first waveform with said carrier waveform to produce a modulated signal that maintains a modulation envelope and frequency information of the first waveform and the carrier waveform; and the carrier waveform; the modulated waveform is capable of transdermally electrically stimulating the predetermined nerve; and
    applying the modulated signal to the mammal's skin.

18. The method according to claim 17, wherein the modulated signal is applied to the mammal's skin in the abdominal or sacral regions of the mammal's body.

19. The method according to claim 17, wherein the first waveform has a frequency substantially within the range of 10-40 Hz, and the carrier waveform has a frequency substantially within the range of 10-400 kHz.

20. The method according to claim 19, wherein the first waveform is a square wave.

21. The method according to claim 20, wherein the carrier waveform is a sinusoidal waveform.

22. The method according to claim 17, further comprising:
    implanting at least one sensor within the mammal's body;
    using the implanted sensor sensing one or more physiological properties within the body;
    wirelessly transmitting biofeedback data representing the sensed physiological properties; and using the biofeedback data to control generation of the first and carrier waveforms by the first and second waveform generators.

23. The method according to claim 22, wherein the biofeedback data is transmitted to a microprocessor that is electrically coupled to and controls the first and second waveform generators.

24. The method according to claim 17, further comprising the step of, prior to the applying step, injecting an electrically conductive gel into a tract within the mammal's body, the tract extending, from a first end substantially at a surface of the skin of the mammal to second end positioned closer to the predetermined nerve, wherein the applying step further comprises applying the modulated waveform at a location substantially in electrical contact with the electrically conductive gel within the first end of the tract.

25. The method according to claim 24, wherein the second end of the tract is positioned substantially adjacent to the predetermined nerve, and wherein the electrically conductive gel substantially fills the tract.

26. The method according to claim 25, wherein the predetermined nerve is the pudendal nerve.

27. A nerve stimulation device comprising:
a first waveform generator adapted to generate a first waveform having a frequency substantially within the range of 10-40 Hz;
a second waveform generator adapted to generate a carrier waveform having a frequency substantially within the range of 10-400 KHz;
an amplitude modulation device electrically coupled to the first and second waveform generators for multiplying the first and carrier waveforms to thereby create a modulated waveform that maintains a modulation envelope and frequency information of the first waveform and the carrier waveform and the carrier waveform; the modulate waveform is capable of transdermally electrically stimulating a predetermined nerve; and
an electrode electrically coupled to the modulation device and positioned substantially adjacent to the skin of a mammal for applying the modulated waveform to the skin of the mammal.

28. The nerve stimulation device according to claim 27, wherein the first and second waveform generators and modulation device are positioned within a patch having an adhesive surface for securing the patch to the skin.

29. The nerve stimulation device according to claim 27, wherein the first waveform is a square wave.

30. The nerve stimulation device according to claim 29, wherein the carrier waveform is a sinusoidal waveform.

31. The nerve stimulation device according to claim 27, further comprising:
a microprocessor electrically coupled to the first and second waveform generators; and
a receiver device electrically coupled to the microprocessor and adapted to receive transmitted biofeedback data and provide the biofeedback data to the microprocessor.

32. The nerve stimulation device according to claim 31, further comprising:
at least one biofeedback device implanted within the mammal, the biofeedback device including at least one sensor adapted to sense one or more physiological properties within the body of the mammal, and at least one transmitter electrically coupled to the sensor and adapted to receive signals representing the sensed physiological properties and transmit biofeedback data representing the sensed physiological properties to a second location.

33. A transdermal stimulation device for selectively stimulating a predetermined body part of a mammal, comprising:
a first waveform generator configured to generate a first analog waveform having a selected amplitude and frequency capable of stimulating the predetermined body part, wherein the generated first waveform is itself incapable of transdermally stimulating the predetermined body part;
a second waveform generator configured to generate a second analog carrier waveform having a selected amplitude and frequency, wherein the frequency of the second carrier waveform is greater than that of the first waveform, wherein the second carrier waveform is capable of passing through the mammal's skin and tissue to reach the predetermined body part, and wherein the frequency of said generated carrier waveform is itself incapable of electrically stimulating the predetermined body part;
an amplitude modulation device electrically coupled to the first and second waveform generators and configured to multiply the second carrier waveform and the first waveform to create a modulated signal that maintains a modulation envelope and frequency information of the first waveform and second carrier waveform, and that is capable of transdermally electrically stimulating the predetermined body part; and
an active electrode electrically coupled to the modulation device and positioned substantially adjacent to the skin of the mammal, the active electrode being configured to apply the modulated signal to the skin.

34. The device according to claim 33, wherein the active electrode is contained within a patch capable of being affixed to the mammal's skin.

35. The device according to claim 33, wherein the predetermined body part is a nerve or a portion of a nerve.

36. The device according to claim 33, wherein the first waveform has a frequency within the range of 10-40 Hz.

37. The device according to claim 36, wherein the second waveform has a frequency within the range of 10-400 kHz.

38. A method for selectively stimulating a predetermined body part of a mammal, comprising:
providing a transdermal stimulation device having a first waveform generator configured to generate a first analog waveform having a selected amplitude and frequency capable of stimulating the predetermined body part, wherein the first waveform is itself incapable of transdermally stimulating the predetermined body part, a second waveform generator configured to generate a second analog carrier waveform having a selected amplitude and frequency, the frequency of the second carrier waveform being greater than that of the first waveform, wherein the frequency of the second carrier waveform is such that it is capable of passing through the mammal's skin and tissue to reach the predetermined body part, but is itself incapable of electrically stimulating the predetermined body part, an amplitude modulation device electrically coupled to the first and second waveform generators and configured to multiply the second carrier waveform and the first waveform to create a modulated signal that maintains a modulation envelope and frequency information of the first waveform and second carrier waveform, an active electrode electrically coupled to the modulation device, the active electrode being adapted to apply the modulated signal to the skin;
positioning the active electrodes substantially adjacent to skin of the mammal; and applying the modulated signal to the mammal's skin via the active electrode to electrically stimulate the predetermined body part.

39. The method according to claim 38, wherein the active electrode is contained within a patch.

40. The method according to claim 39, wherein the positioning step further comprises placing the patch substantially in an abdominal or sacral region of the mammal 41. The method according to claim 38, wherein the predetermined body part is a nerve, or a portion of a nerve.

42. The method according to claim 38, wherein the first waveform has a frequency within the range of 10-40 Hz.

43. The method according to claim 42, wherein the second waveform has a frequency within the range of 10-400 kHz.

* * * * *